US008866086B2

(12) United States Patent
Michel et al.

(10) Patent No.: US 8,866,086 B2
(45) Date of Patent: Oct. 21, 2014

(54) PET SCANNER WITH EMISSION AND TRANSMISSION STRUCTURES IN A CHECKERBOARD CONFIGURATION

(75) Inventors: Christian J. Michel, Lenoir City, TN (US); Maurizio Conti, Knoxville, TN (US); Ronald Grazioso, Knoxville, TN (US); Piotr Szupryczynski, Knoxville, TN (US); A. Andrew Carey, Lenoir City, TN (US); Larry Byars, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 238 days.

(21) Appl. No.: 13/198,804

(22) Filed: Aug. 5, 2011

(65) Prior Publication Data

US 2013/0032721 A1 Feb. 7, 2013

(51) Int. Cl.
*G01T 1/164* (2006.01)
*G01T 1/20* (2006.01)
*G01T 1/202* (2006.01)
*G01T 1/161* (2006.01)

(52) U.S. Cl.
CPC .............. *G01T 1/1615* (2013.01); *G01T 1/202* (2013.01)
USPC .................. 250/363.03; 250/361 R; 378/4

(58) Field of Classification Search
USPC ................ 250/363.03, 361 R; 378/4
See application file for complete search history.

(56) References Cited

U.S. PATENT DOCUMENTS

| | | | | |
|---|---|---|---|---|
| 5,629,971 A | * | 5/1997 | Jones et al. | 378/145 |
| 5,750,991 A | * | 5/1998 | Moyers et al. | 250/363.03 |
| 6,774,370 B1 | * | 8/2004 | Uchida et al. | 250/363.03 |
| 7,601,963 B2 | | 10/2009 | Aykac et al. | |
| 2003/0107000 A1 | * | 6/2003 | Yamashita et al. | 250/363.03 |
| 2004/0036026 A1 | * | 2/2004 | Engdahl et al. | 250/363.09 |
| 2010/0102813 A1 | * | 4/2010 | Schulz et al. | 324/309 |
| 2010/0108896 A1 | * | 5/2010 | Surti et al. | 250/363.04 |
| 2011/0101229 A1 | * | 5/2011 | Inadama et al. | 250/367 |
| 2011/0210255 A1 | * | 9/2011 | Kim et al. | 250/362 |
| 2012/0039446 A1 | * | 2/2012 | Cui et al. | 378/149 |
| 2012/0236987 A1 | * | 9/2012 | Ruimi et al. | 378/19 |

FOREIGN PATENT DOCUMENTS

| WO | WO 2010041313 | * | 4/2010 |
|---|---|---|---|
| WO | WO 2010041313 A1 | * | 4/2010 |

OTHER PUBLICATIONS

Thompson et al., A Central Positron Source to Perform the Timing Alignment of Detectors in a PET Scanner, Oct. 2005, IEEE Transactions on Nuclear Science, vol. 52, No. 5, pp. 1300-1304.*
David W. Townsend et al., A Rotating PET Scanner Using BGO Block Detectors: Design, Performance and Applications, 34 J Nucl Med 1367-1376 (1993).

(Continued)

*Primary Examiner* — Casey Bryant
*Assistant Examiner* — Jeremy S Valentiner
(74) *Attorney, Agent, or Firm* — Peter Kendall

(57) ABSTRACT

Apparatuses, computer-readable mediums, and methods are provided. In one embodiment, a positron emission tomography ("PET") detector array is provided which includes a plurality of crystal elements arranged in a two-dimensional checkerboard configuration. In addition, there are empty spaces in the checkerboard configuration. In various embodiments, the empty spaces are filled with passive shielding, transmission source assemblies, biopsy instruments, surgical instruments, and/or electromagnetic sensors. In various embodiments, the crystal elements and the transmission source assemblies simultaneously perform emission/transmission acquisitions.

13 Claims, 9 Drawing Sheets

(56) References Cited

OTHER PUBLICATIONS

C J Thompson et al., Feasibility of Using Beta-Gamma Coincidence for 3D PET Attenuation Correction, 47 IEEE Transactions on Nuclear Science, 1176-1181 (2002).

Marie-Laure Camborde et al., Use of Beta-Gamma Coincidence Detection to Improve the Quality of Transmission Scans for PET, Medical Physics Unit, McGill University, Montreal (Sep. 2001).

Johan Nuyts et al., Simultaneous Maximum A-Posteriori Reconstruction of Attenuation and Activity Distributions from Emission Sinograms, 18 IEEE Trans Med Imaging, 393-403 (1999).

C.C. Watson et al., Design and Performance of a Single Photon Transmission Measurement for the ECAT ART, 48 IEEE Trans. Nucl. Sci., 673-679 (1998).

* cited by examiner

PET SCANNER WITH EMISSION AND TRANSMISSION STRUCTURES IN A CHECKERBOARD CONFIGURATION

BACKGROUND

1. Field of the Invention

Embodiments of the present invention generally relate to nuclear medicine, and systems for obtaining images of a patient's body organs of interest. In particular, the present invention relates to novel methods, apparatuses, computer readable mediums, and systems for reducing the number of radiation detectors used to cover a given axial field of view.

2. Description of the Related Art

Nuclear medicine is a unique medical specialty wherein radiation is used to produce images that show the function and anatomy of organs, bones and/or tissues of the body. Radiopharmaceuticals are introduced into the body, either by injection, inhalation, or ingestion, and are attracted to specific organs, bones and/or tissues of interest. For example, the radiopharmaceutical (e.g., rubidium) is injected into the bloodstream to image cardiac blood flow.

The radiopharmaceutical produces gamma photon emissions that emanate from the body. One or more detectors are used to detect the emitted gamma photons and the information collected from the detector(s) is processed to calculate the position of origin of the emitted photon from the source (i.e., the body organ or tissue under study). The accumulation of a large number of events (e.g., a single gamma when using Single Photon Emission Computed Tomography ("SPECT") and coincident gamma events when using Positron Emission Tomography ("PET")) allows an image of the organ or tissue under study to be displayed.

FIG. 1 shows a system 100 which includes a known apparatus 102 for superposed MR and PET imaging. The apparatus 102 includes a known MR tube 104. The MR tube 104 defines a longitudinal direction Z (not shown), parallel to a longitudinal axis of a patient (also not shown), which extends orthogonally with respect to the plane of the drawing in FIG. 1.

As shown in FIG. 1, a plurality of PET detector units 106 arranged in pairs opposite each other about the longitudinal direction z are arranged coaxially within the PET scanner 104. The PET detector units 106 preferably include an Avalanche photodiode ("APD") array 108 with an upstream array of Lutetium Oxyorthosilicate ("LSO") crystals 110 and an electrical amplifier circuit ("AMP") 112.

A computer 120 is also included in the system 100. The computer 120 includes a central processing unit ("CPU") 114 for image processing of superposed MR and PET imaging, a user interface 118 (depicted as a keyboard), and a monitor 116 for viewing input and output data.

A PET scanner utilizes a large number of detectors (typically organized in blocks of scintillators) arranged around the patient in rings or in panels covering the largest possible solid angle. Scintillator material and associated photo-detectors and electronic channels are expensive.

In order to reduce cost, two approaches have been used, but both come with shortcomings: one approach is to shorten the length of the scintillator (e.g., to shorten the length from 2 cm to about 1.5 cm) and the second approach is to use a partial ring rotating tomograph (e.g., as described in David W. Townsend et al., A Rotating PET Scanner Using BOO Block Detectors: Design, Performance and Applications, 34 J Nucl Med 1367-1376 (1993)). Shortening the length of the crystal reduces the efficiency of the crystal (e.g., shortening the length of the crystal by 20% also reduces the efficiency of the crystal by 20%) and requires building new block detectors (which is relatively expensive).

Thus there is a need in the art for a lower cost scanner with substantially the same axial field-of-view ("FOV") (with little or no detector or gantry motion), re-configuration of existing PET/CT scanners into a lower cost scanner with substantially the same axial FOV (with little or no detector or gantry motion), and a PET scanner with transmission capability (with no requirement of computerized tomography ("CT") or magnetic resonance ("MR") for attenuation purposes).

SUMMARY

These and other deficiencies of the prior art are addressed by embodiments of the present invention, for obtaining images of a patient's body organs of interest. Embodiments of the present invention generally relate to nuclear medicine, and systems for obtaining images of a patient's body organs of interest. For example, embodiments of the present invention relate to novel methods, apparatuses, computer readable mediums, and systems for reducing the number of radiation detectors used. In one embodiment of the invention, a scintillation detector is provided which includes a plurality of elements arranged in a two-dimensional checkerboard configuration. In addition, there are empty spaces in the checkerboard configuration. In various embodiments, these empty spaces are filled with passive shielding, transmission source assemblies, biopsy instruments, surgical instruments, and/or electromagnetic sensors. In various embodiments, the detector blocks and the transmission source assemblies simultaneously perform emission/transmission acquisitions.

The axial coverage using the checkerboard configuration is substantially the same as a fully populated ring scanner. The checkerboard pattern eliminates a fraction of the data at the cost of reducing data redundancy, and a fraction of the sensitivity of the scanner in emission mode. By removing about one third of the blocks there is a decrease in the emission sensitivity by about fifty percent while maintaining a substantially same axial FOV as an array that is fully populated with emission blocks. In various embodiment, more sparseness in the emission data collection may be allowed when time-of-flight (TOF) is used, because of the additional information associated with the TOF data.

BRIEF DESCRIPTION OF THE DRAWINGS

So that the manner in which the above recited features of the present invention can be understood in detail, a more particular description of the invention, briefly summarized above, can be had by reference to embodiments, some of which are illustrated in the appended drawings. It is to be noted, however, that the appended drawings illustrate only typical embodiments of this invention and are therefore not to be considered limiting of its scope, for the invention can admit to other equally effective embodiments.

To facilitate understanding, identical reference numerals have been used, wherever possible, to designate identical elements that are common to the figures.

DETAILED DESCRIPTION

Figure 1:
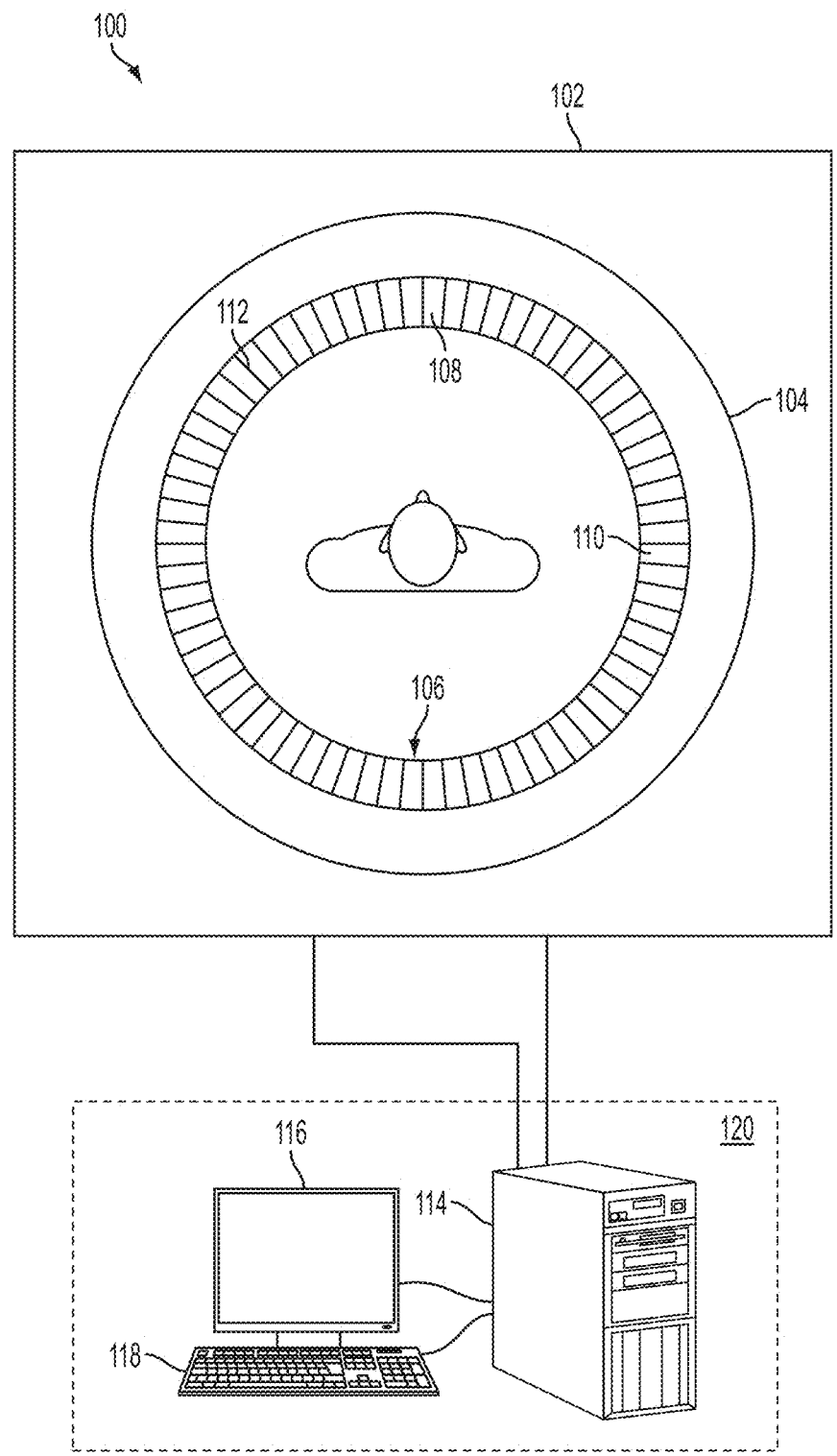
FIG. 1 is a prior art embodiment of an imaging appliance.

In the following description, numerous specific details are set forth to provide a more thorough understanding of the invention. As will be apparent to those skilled in the art, however, various changes using different configurations can be made without departing from the scope of the invention. In other instances, well-known features have not been described in order to avoid obscuring the invention. Thus, the invention is not considered limited to the particular illustrative embodiments shown in the specification and all such alternate embodiments are intended to be included in the scope of the appended claims.

Various exemplary embodiments will now be described more fully with reference to the accompanying drawings in which only some exemplary embodiments are shown. Specific structural and functional details disclosed herein are merely representative for purposes of describing example embodiments. The present invention, however, can be embodied in many alternate forms and should not be construed as limited to only the example embodiments set forth herein.

It will be understood that when an element is referred to as being "connected," or "coupled," to another element, it can be directly connected or coupled to the other element or intervening elements can be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted can occur out of the order noted in the figures. For example, two figures shown in succession can in fact be executed substantially concurrently or can sometimes be executed in the reverse order, depending upon the functionality/acts involved.

Spatially relative terms, such as "beneath", "below", "lower", "above", "upper", and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device can be otherwise oriented (rotated 90 degrees or at other orientations) and the spatially relative descriptors used herein are interpreted accordingly.

Although the terms first, second, etc. can be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Aspects of the invention utilize a PET scanner architecture, which includes block detectors assembled in rings or panels around the patient, but in which part of the detectors have been removed according to a checkerboard structure or alternating pattern. In various embodiments, the missing detectors can be fully or partially replaced by transmission sources, allowing simultaneous emission-transmission acquisitions. In yet other embodiments, the missing detectors can be replaced with other devices (e.g., electromagnetic sensors, ultrasonic, and/or biopsy instrumentation). Aspects of the invention are not restricted to PET detector units utilizing an APD photodiode array and an array of LSO crystals; rather, other types of photodiodes, crystals and apparatuses can be used in accordance with embodiments of the invention. For example, in various embodiments, Bismuth Germanate (i.e., Bismuth Germanium Oxide or "BGO") or any scintillator crystal, phototubes, APD, or Silicon Photomultiplier tube ("SiPM") can used in accordance with aspects of the invention.

Generally, decreasing the number of detectors also decreases the sensitivity (i.e., the efficiency with respect to an instrument that is fully populated with detectors). The number of detectors removed (and the resulting sensitivity) can vary with the degree of sensitivity needed for analysis. For example, a higher sensitivity can be used for imaging of a brain (i.e., more detectors) than for a small animal or a limb (e.g., a human leg). In addition, more detectors can be removed when a scanner utilizes time-of-flight ("TOF") data than in a scanner that utilizes non-TOF data. Aspects disclosed herein can, in various embodiments, be used with standalone single modality or multi-modality imaging devices.

Figure 2:
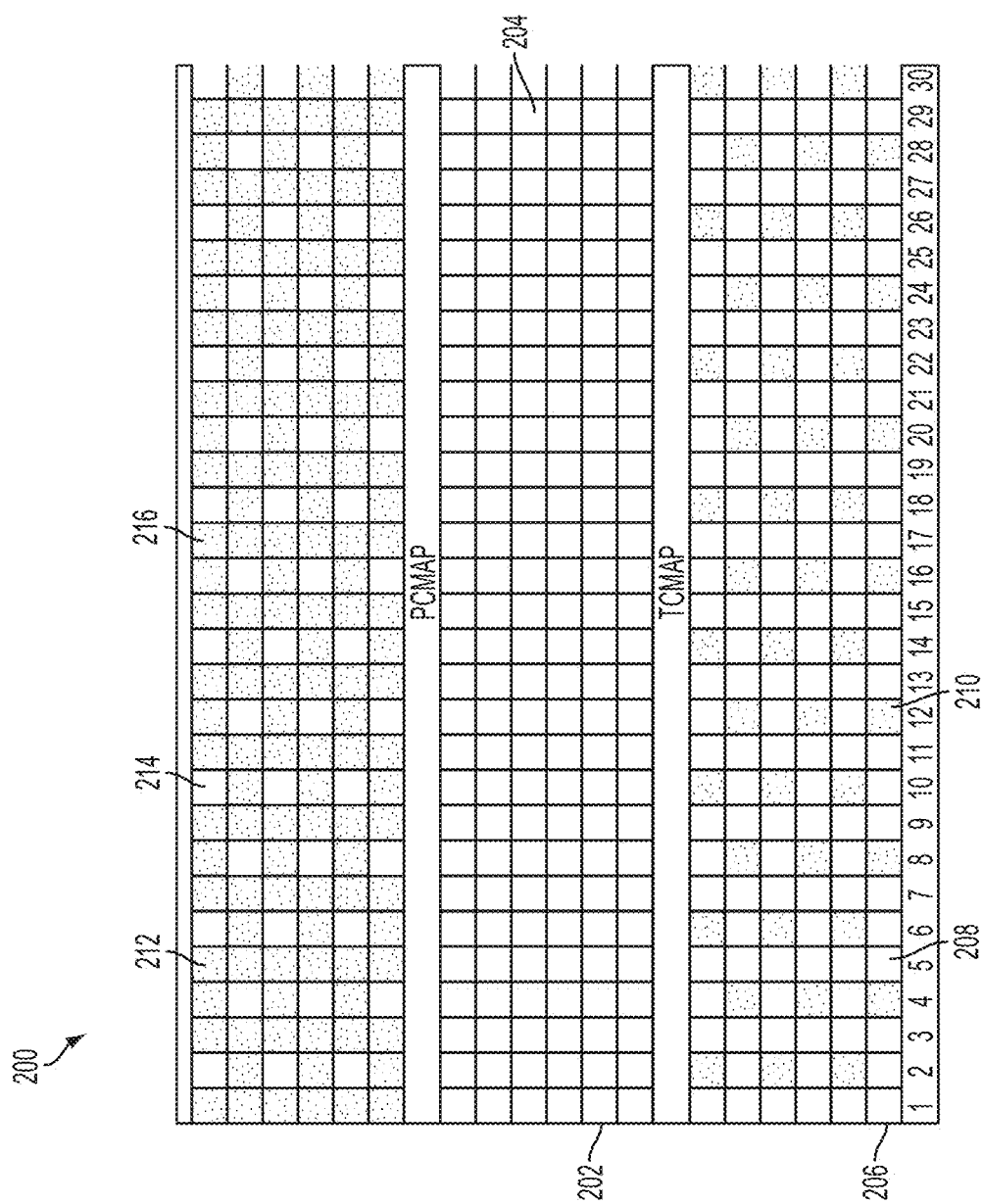
FIG. 2 depicts a juxtaposition of a fully populated detector array, an embodiment of a checkerboard emission configuration, and an embodiment of a complementary transmission configuration in accordance with embodiments of the invention.

FIG. 2 depicts a juxtaposition 200 of a fully populated detector array, an embodiment of a checkerboard emission configuration, and an embodiment of a complementary checkerboard transmission configuration according to aspects of the invention. The checkerboard configuration disclosed herein is a two-dimensional checkerboard configuration. For illustrative purposes only, FIG. 2 is divided into three sections (i.e., a complete detector array 202, a checkerboard emission configuration 206, and a complementary checkerboard transmission configuration 212). In juxtaposition 200, white spaces indicate the presence of some type of component (e.g., a detector crystal, passive shielding (e.g., lead, tungsten, gold, depleted uranium, or tungsten polymer), cameras, electromagnetic sensors, biopsy instrumentation, and/ transmission source assemblies). When an emission block is removed, the space left by the removed emission block is available for another type of component.

Specifically, detector array 202 is depicted as a fully populated array of detector blocks 204 (e.g., all 192 blocks populated with detectors). For illustrative purposes only, the checkerboard emission configuration 206 and the complementary checkerboard transmission configuration 212 are juxtaposed with the detector array 202. This juxtaposition is used to show that the checkerboard emission configuration 206 and checkerboard transmission configuration 212 are complementary.

In checkerboard emission configuration 206, some of the detector blocks 204 have been removed. Blocks that have been removed from the checkerboard emission configuration 206 are indicated as empty spaces 210 (and are depicted as shaded blocks). In the checkerboard emission configuration 206, the remaining detector blocks are referred to as emission blocks 208. The emission blocks 208 and empty spaces 210 are arranged in a checkerboard fashion in both orthogonal X and Y directions for each row and each column in a given horizontal layer of the checkerboard emission configuration 206 throughout the orthogonal Z dimension of the detector. Other elements/instruments can be put in the empty spaces 210. (e.g., passive shielding (e.g., lead, tungsten, gold, depleted uranium, or tungsten polymer), cameras, electromagnetic sensors, biopsy instrumentation, surgical instruments, and/ transmission source assemblies.

For illustrative purposes only, about one third of the emission blocks 208 have been removed (i.e., a removal of about 48 of the 192 blocks). Although the number of emission blocks 208 has been reduced in the emission configuration 206, the axial coverage (i.e., FOV) is relatively the same as in the fully populated detector array 202. The empty spaces 210 and emission blocks 208 form a checkerboard pattern that eliminates a fraction of the coincidence data while still allowing imaging in the full FOV.

Reducing the number of emission blocks 208 also reduces the sensitivity of the scanner in emission mode while maintaining a substantially same axial FOV as an array that is fully populated with emission blocks. Reducing the number of emission blocks 208 also reduces the cost of the scanner. Further, pre-existing scanners can be re-configured into a new low-cost scanner with substantially the same axial FOV but reduced sensitivity, by removing emission blocks 208 in the checkerboard pattern. Alternatively, an existing scanner can use the checkerboard configuration to extend the FOV.

In various embodiments of the invention, an empty space 210 can be adjacent to another empty space 210.

"Reconfiguration" as used herein means removing some blocks used for gamma detection in a well defined pattern which allows complete sampling in image space. By removing about one third of the emission blocks 208 the emission sensitivity decreases by about 50 percent.

By reducing the number of emission blocks 208 in a checkerboard pattern, artifact-free emission images can be produced utilizing a non-TOF scanner. In various embodiments, more emission blocks 208 can be removed in a TOF scanner than in a non-TOF scanner because of the additional information associated with TOF data (in a TOF scanner).

In addition to cost reduction, there are other advantages associated with having emission blocks 208 and empty spaces 210, arranged in a checkerboard configuration, in the ring or panel architecture. For example, in various embodiments, some/all of the empty spaces 210 can be replaced with passive shielding (e.g., lead, tungsten, gold, depleted uranium, or tungsten polymer), cameras, electromagnetic sensors, biopsy instrumentation, and/or transmission source assemblies.

Although FIG. 2 is depicted and described as having about one third of the emission blocks 208 removed, that is for illustrative purposes only. Fewer or more emission blocks 208 can be present in the checkerboard configuration. The percentage of emission blocks 208 remaining in the checkerboard pattern depends upon several factors. For example, the type of emission blocks 208 used (and the FOV associated with the emission blocks 208, the sensitivity needed, the body part being examined, and/or whether a scanner acquires additional data (e.g., a TOF scanner acquires more data than a non-TOF scanner). For example, in some examination procedures a brain would typically need a higher sensitivity than a small animal or human femur. Because the small animal or human femur wouldn't need as much sensitivity, a smaller percentage of emission blocks 208 can be used, in the checkerboard pattern, when scanning the femur or small animal. In addition, an even smaller percentage of emission blocks 208 can be used in a TOF scanner than in a non-TOF scanner.

Typically, the sensitivity, in the axial direction, of a PET scanner is a triangular function. The sensitivity is at its maximum (i.e., peaks) in the center of the triangle and is parallel to the Z axis. When performing a multi-mode acquisition the different acquisitions are overlapped to make a uniform sensitivity in the axial direction for the whole body. Aspects disclosed herein can be used to modify the axial sensitivity profile (i.e., make the sensitivity profile flatter) of the scanner to make the scanner more equalized (as opposed to peaking at the center and having the triangular function) in the Z direction. The modified axial sensitivity profile reduces the need for overlapping and would allow faster scanning.

As indicated above, in emission configuration 206, empty spaces 210 indicate where emission blocks 208 have been removed. In the complementary checkerboard transmission configuration 212, the empty spaces 210 (in the emission configuration 206) have been replaced with complementary transmission source elements 214.

Also depicted in the complementary checkerboard transmission configuration 212 are blocks that are the remaining emission blocks in the checkerboard emission configuration 206 (depicted as shaded blocks 216 in the complementary checkerboard transmission configuration 212). The emission blocks 216 are shaded, in the complementary checkerboard transmission configuration 212, for viewing contrast against the transmission source element blocks 214 and to show the complementary relationship between the checkerboard emission configuration 206 and the complementary transmission source configuration 212. In short, lead lines 204, 208, and 216 depict emission blocks.

Figure 3:
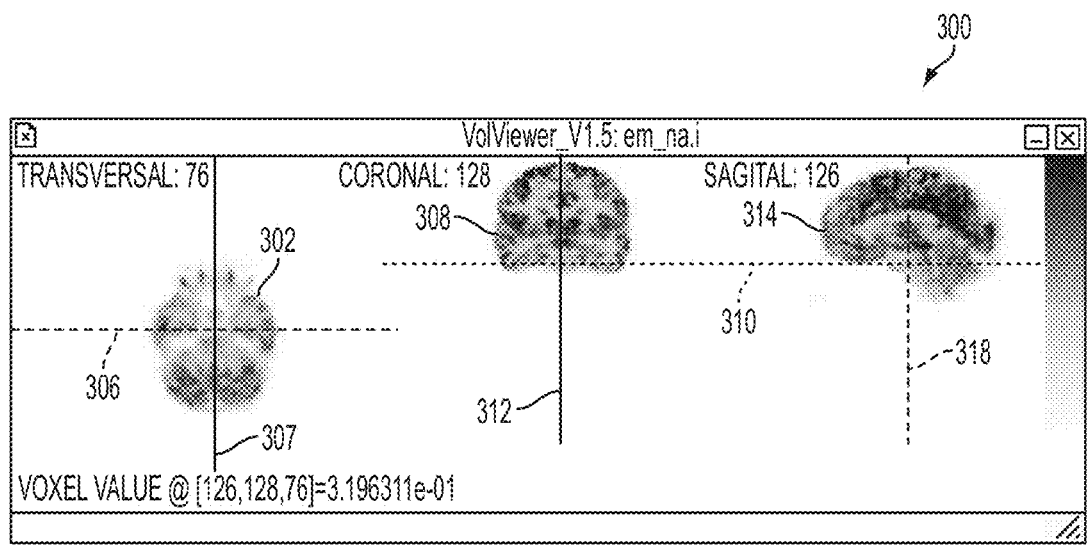
FIG. 3 depicts a series reconstructed images, without scatter correction, in accordance with the prior art.

FIG. 3 is a series of reconstructed images 300, without scatter correction, in accordance with the prior art. Specifically, FIG. 3 depicts a top view 302 of a brain, a front view 308 of the brain, and a side view 314 of the brain. Views 302, 308, and 314 are reconstructed images using all of the detectors (e.g., using 192 detectors). Lead line 306 denotes an "X" axis and lead line 307 denotes a "Y" axis for the top view 302 of the brain. Lead line 310 denotes the "X" axis and lead lines 312 and 318 denote a "Z" axis (parallel to the longitudinal axis of a patient bed (not shown).

For continuity, in FIGS. 4, 6, and 7-9 below, "X," "Y," and "Z" axes are depicted with lead lines 306, 310, 312, and 318. The depiction of theses axes and the attached lead lines is the same as that depicted and described above with respect to FIG. 3. As such, a description of the "X," "Y," and "Z" axes is not repeated below.

Figure 4:
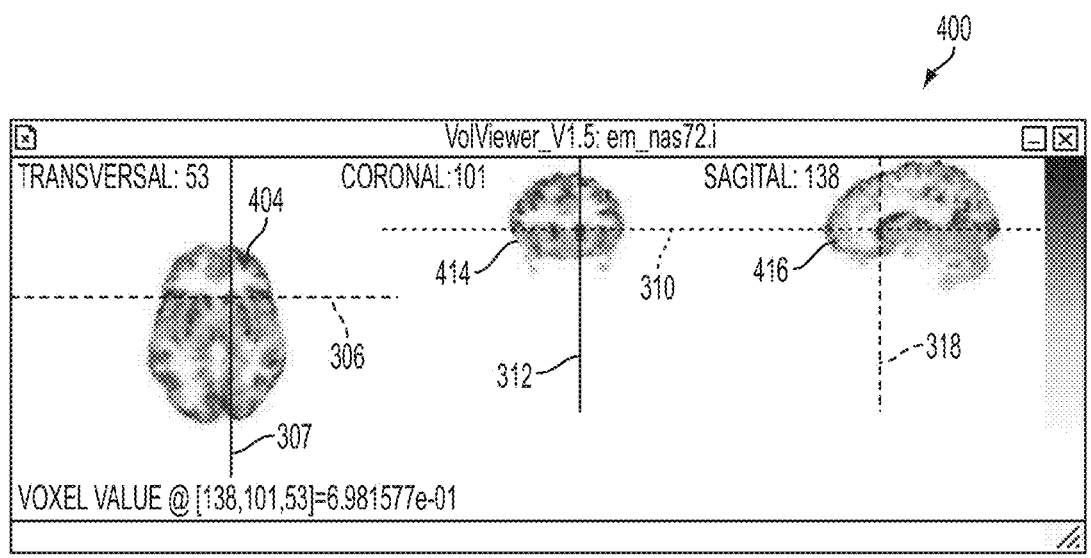
FIG. 4 depicts a series of reconstructed images, with scatter correction, in accordance with the prior art.

FIG. 4 depicts a comparison of a series of reconstructed images with none of the detector blocks missing (e.g., 192 detector blocks) and with scatter correction, in accordance with the prior art. Specifically, FIG. 4 depicts a top view 404 of a brain, a front view 414 of the brain, and a side view 416 of the brain. Views 302, 308, and 314 are reconstructed images using virtually all of the detectors (e.g., using 191 out of 192 detectors). Scatter correction, in FIG. 4, provides images with greater contrast (i.e., sharper images) than images without scatter correction (i.e., the images in FIG. 3).

Figure 5:
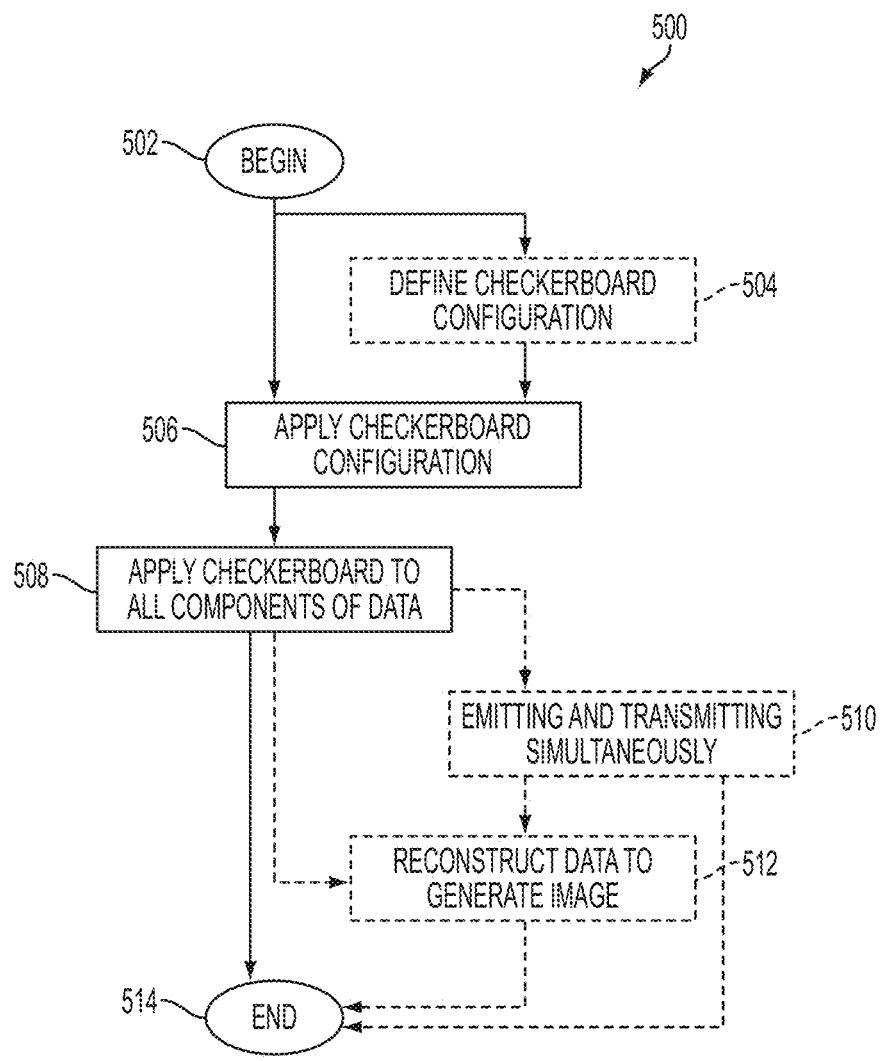
FIG. 5 depicts an embodiment of a method for utilizing a checkerboard configuration in accordance with embodiments of the invention.

FIG. 5 depicts an embodiment of a method 500 in accordance with embodiments of the invention. Specifically, method 500 begins at step 502 and proceeds towards optional step 504, in some embodiments. In other embodiments, the method 500 begins at step 502 and proceeds towards step 506.

In various embodiments, the method 500 begins at step 502 and proceeds towards optional step 504. At optional step 504, a checkerboard configuration is defined. In the checkerboard configuration, some blocks are selected as emission blocks. The empty spaces can be replaced with passive shielding (e.g., lead, tungsten, gold, depleted uranium, or tungsten polymer), cameras, electromagnetic sensors, biopsy instrumentation, and/or transmission source assemblies. For illustrative purposes, the empty spaces are transmission source assemblies (i.e., transmission blocks). The checkerboard configuration is selected such that redundancy is reduced and sensitivity is sufficient for image analysis.

In various embodiments, the detectors selected for removal are randomly (i.e., either by a user or processor) selected. In other embodiments, the detectors, selected for removal, are manually selected non-adjacent detectors and geographically scattered throughout the detector array. After optional step 504, the method 500 proceeds towards step 506.

At step 506, a checkerboard configuration is applied. Data from detectors are used in accordance with the checkerboard configuration. In various embodiments, the checkerboard configuration is selected from memory. A "checkerboard configuration" as used herein is defined as a group of detectors selected to be ignored, from an entire array of detectors, to reduce sensitivity and provide a substantially same axial FOV as the entire array of detectors. For example, in various embodiments, about of a third of the detectors can be removed from the emission data. In short, the checkerboard configuration is used to determine whether a block is used for emission (and in various embodiments whether the remaining blocks are used for transmission). Thereafter, the method 500 proceeds towards step 508.

At step 508, the checkerboard configuration is applied to components of the image data (i.e., to true coincidences). For example, the checkerboard configuration is applied to prompt, normalization (or sensitivity), delay, scatter, and attenuation components. The data associated with non-emission blocks are ignored during component analysis. In various embodiments, after step 508, the method 500 proceeds towards optional step 510, optional step 512, or ends at step 514.

In various embodiments, after step 508, the method 500 proceeds towards optional step 510. At step 510, simultaneous emission (by EE coincident blocks) and transmission (by ET coincident blocks) occurs. In various embodiments, after simultaneous emission/transmission at optional step 510, the method 500 proceeds towards optional step 512 and in other embodiments, after optional step 510 the method 500 proceeds towards and ends at step 514.

At optional step 512, an image is generated from the data. After optional step 512, the method 500 proceeds towards and ends at step 514.

Figure 6:
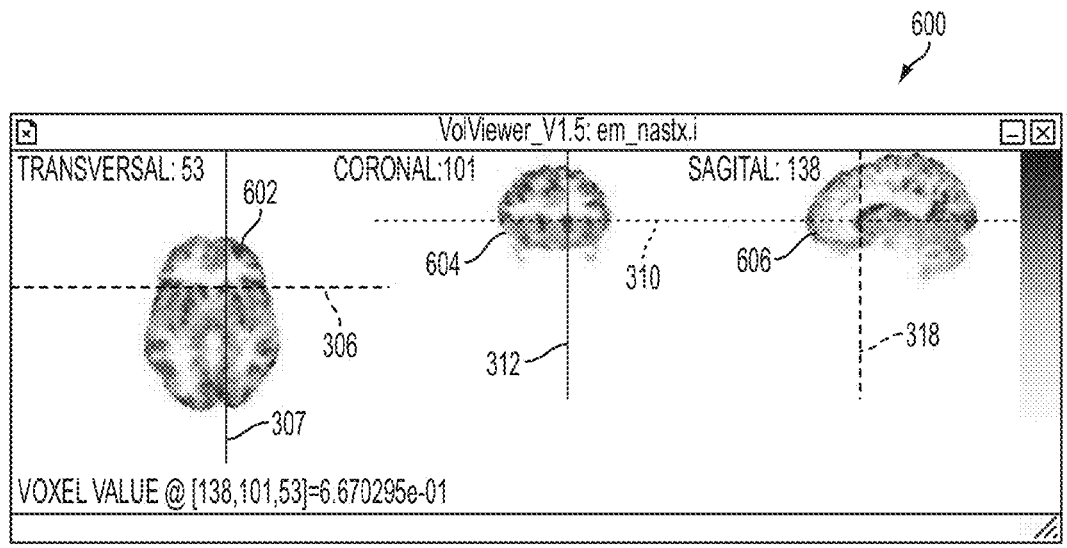
FIG. 6 depicts a series of reconstructed images in accordance with embodiments of the invention.

FIG. 6 depicts a series of reconstructed images 600 in accordance with embodiments of the invention. Specifically, FIG. 6 depicts a top view 602 of a brain, a front view 604 of the brain, and a side view 606 of the brain. Views 602, 604, and 606 are reconstructed images that were generated with about one third of the detector blocks (e.g., about 48 Emission blocks out of 192 replaced with Transmission blocks) removed. Reducing the number of coincidence blocks also reduces the sensitivity of images (i.e., the images depicted in views 602, 604, and 606). Although about a third of the detector blocks were removed to generate the images depicted in views 602, 604, and 606, that depiction is for illustrative purposes only. In various embodiments of the invention, more or less detector blocks can be ignored. The percentage of detector blocks removed would depend upon a sensitivity desired for an intended analysis.

Figure 7:
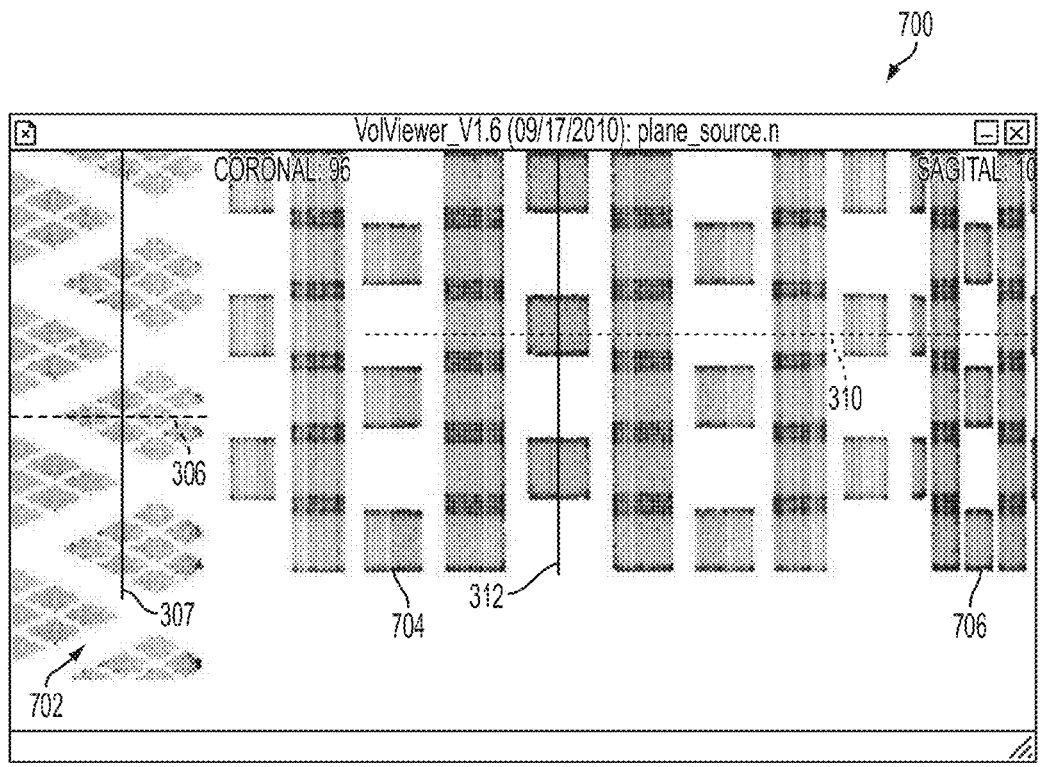
FIG. 7 depicts projection data, in sonogram space from an orthogonal viewer, in accordance with embodiments of the invention.

FIG. 7 depicts projection data 700, in sonogram space from an orthogonal viewer, in accordance with embodiments of the invention. The projection data 702 is used to produce the reconstructed image depicted as top view 602. The projection data 704 is used to produce the reconstructed image depicted by front view 604. The projection data 706 is used to produce the reconstructed image depicted by side view 606. White spaces in projection data 702, 704, and 706 indicate that there is no information for those block-blocks (i.e., a pair of blocks in coincidence with each other) and a loss in sensitivity.

Transmission acquisitions are necessary in PET imaging to correct attenuation of an emission image. Most PET scanners are coupled to a CT system to obtain attenuation (aka "mu") maps. However, the inclusion of CT equipment can add additional cost to an examination procedure and subject a patient to a high additional dose of radiation.

Aspects of the invention do not require the addition of CT equipment to the PET system. The missing detector blocks 210 can be fully or partially replaced by transmission coincidence sources, allowing simultaneous emission/transmission acquisitions. Interleaving transmission source assemblies with the detector blocks 208 by inserting the transmission source assemblies into the empty spaces left by the missing detector blocks 210 provides several advantages. For example, this improvement over the prior art provides a low cost alternative to CT; a reliable mu map to correct inaccuracies in the MR mu map; and at the same time allows performing simultaneous emission (EM) and transmission (TX) acquisition, since the TX and EM detectors cover the same field of view.

For example, in the checkerboard configuration, of FIG. 2, with a head insert for a circular array (having 32 heads with 6 blocks per head), the pattern repeats itself every 4 heads. The exemplary pattern is as follows (where an "E" block is an emission block and a "T" block is a transmission block): one regular head (6 E blocks), a mixed head (ETETET), another regular head (6 E blocks), and a minor mixed head (TE- TETE). In this example, two types of coincident events are possible: an emission (EE) event and a transmission (ET) event.

The transmission event is a beta-gamma coincidence. In various embodiments, the T block can be composed of several weak positron transmission sources (e.g. a few microCi of Ge-68 per source) each embedded in a scintillator having a fast decay constant of about 2 ns (e.g., a plastic scintillator). A plastic scintillator (having about 6 mm on each side (i.e., a cube of about 6 mm by about 6 mm by about 6 mm)), is quasi insensitive to gamma rays and above 90% efficient to positron detection from Ge-68 (max Energy=1.9 MeV). Compared to the traditional gamma-gamma transmission mode, the beta gamma mode is estimated to be about 3 times more efficient (assuming 30% detection efficiency for the near gamma detector).

When surrounding the Tx sources with a tungsten wall of about 7.5 mm, the interaction probability (integrated between about 100 and about 511 keV) in a neighboring block is about 1.1% or about 0.5% when blocks are facing or touching with a corner, respectively. Assuming 2 microCi per source, i.e. 18 microCi per block, the worse case is an additional singles rate of 13 kcps in some E blocks, which adds to the LSO background (about 6 kcps). In various embodiments, a Tx block can be coupled to a silicon photo-multiplier ("SiPM") array or a photo-multiplier tube.

Note that the T blocks associated with aspects of the invention are not retractable, so the sources (about 48×18 microCi) are exposing the patient to more radiation than with LSO only. Transmission can be measured separately from emission or simultaneously. Scatter in Tx can be simulated and subtracted. Alternatively the contaminated mu-map can be segmented and re-labeled. In a scanner with TOF capability, scatter can be rejected if the TOF does not correspond to the chord length. The transmission technique disclosed herein is different than the transmission technique proposed by C J Thompson, Feasibility of Using Beta-Gamma Coincidence for 3D PET Attenuation Correction, IEEE TRANSACTIONS ON NUCLEAR SCIENCE, VOL. 47, Issue 3, 1176-1181 (August 2002) ("Thompson"). The Thompson reference discloses using retractable sources and a Tx source distribution that requires motion.

In various embodiments, only a small fraction of the E blocks and incomplete Tx data helps to stabilize the solution of the completion of the mu-map using MLLA technique (see Johan Nuyts et al., "Simultaneous Maximum A-Posteriori Reconstruction of Attenuation and Activity Distributions from Emission Sinograms", *IEEE Trans Med Imaging,* 1999; 18 (5): 393-403), provide better/correct mu-values for critical compartments of the segmented MR image (e.g., of the lungs which is from a whole body MR-PET device).

Figure 8:
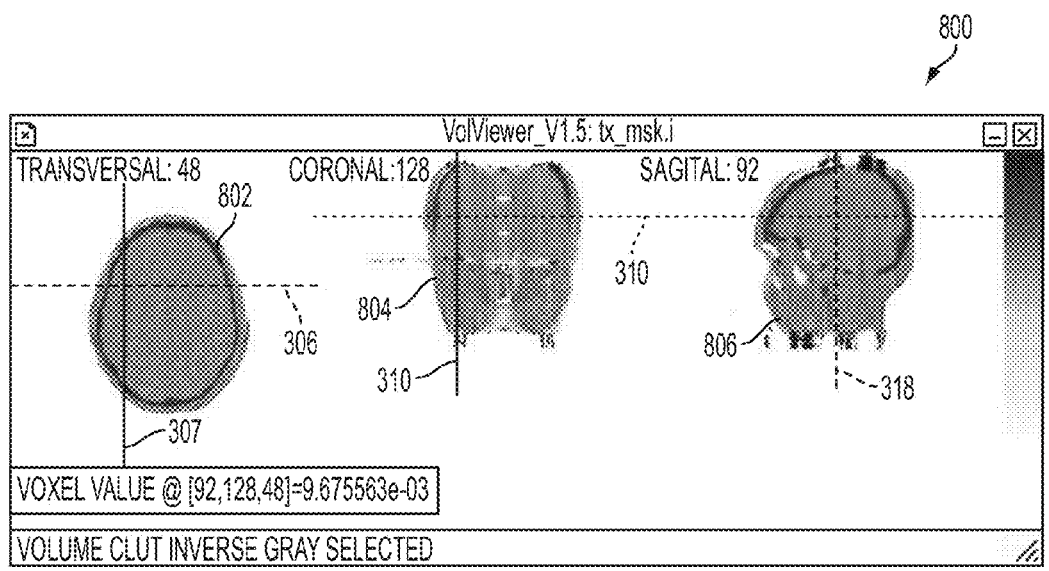
FIG. 8 depicts a series of transmission images in accordance with embodiments of the invention.

FIG. 8 depicts a series of transmission images/mu maps 800 of a human head in accordance with embodiments of the invention. Specifically, the comparison 800 includes a top view attenuation image 802, a front view attenuation image 804, and a side view attenuation image 806. The attenuation images 802, 804, and 806 were created from 48 transmission blocks in coincidence with opposite emission blocks.

Figure 9:
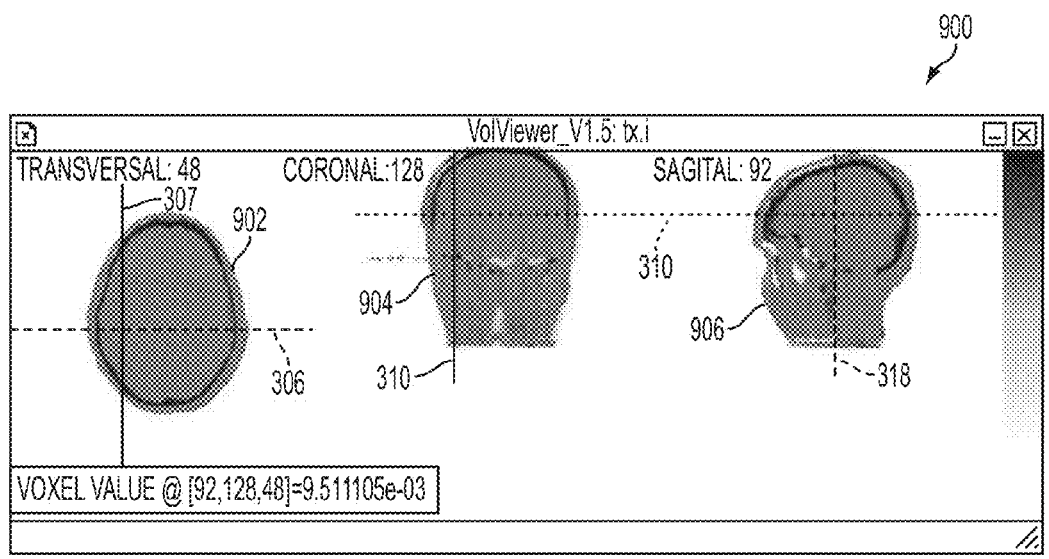
FIG. 9 depicts a series of transmission images in accordance with the prior art.

FIG. 9 depicts a series of transmission images/mu maps 900 of a human head in accordance with the prior art. Specifically, FIG. 9 depicts top view attenuation image 902, front view attenuation image 904, and side view attenuation image 906 are provided in accordance with the prior art. Specifically, mu images 902, 904, and 906 were generated using a rotating source and all 192 emission blocks in coincidence. However, there are several steps to generate mu images 902, 904, and 906. First, a "blank scan" (i.e., a rotating scan with no object in the FOV) is performed; then a transmission scan (i.e., a rotating scan with the object in the FOV) is performed; thereafter a ratio of the blank scan to transmission scan is used to create an attenuation projection; and the logarithm of the attenuation projection is reconstructed to create the mu images 808, 810, and 812.

Figure 10:
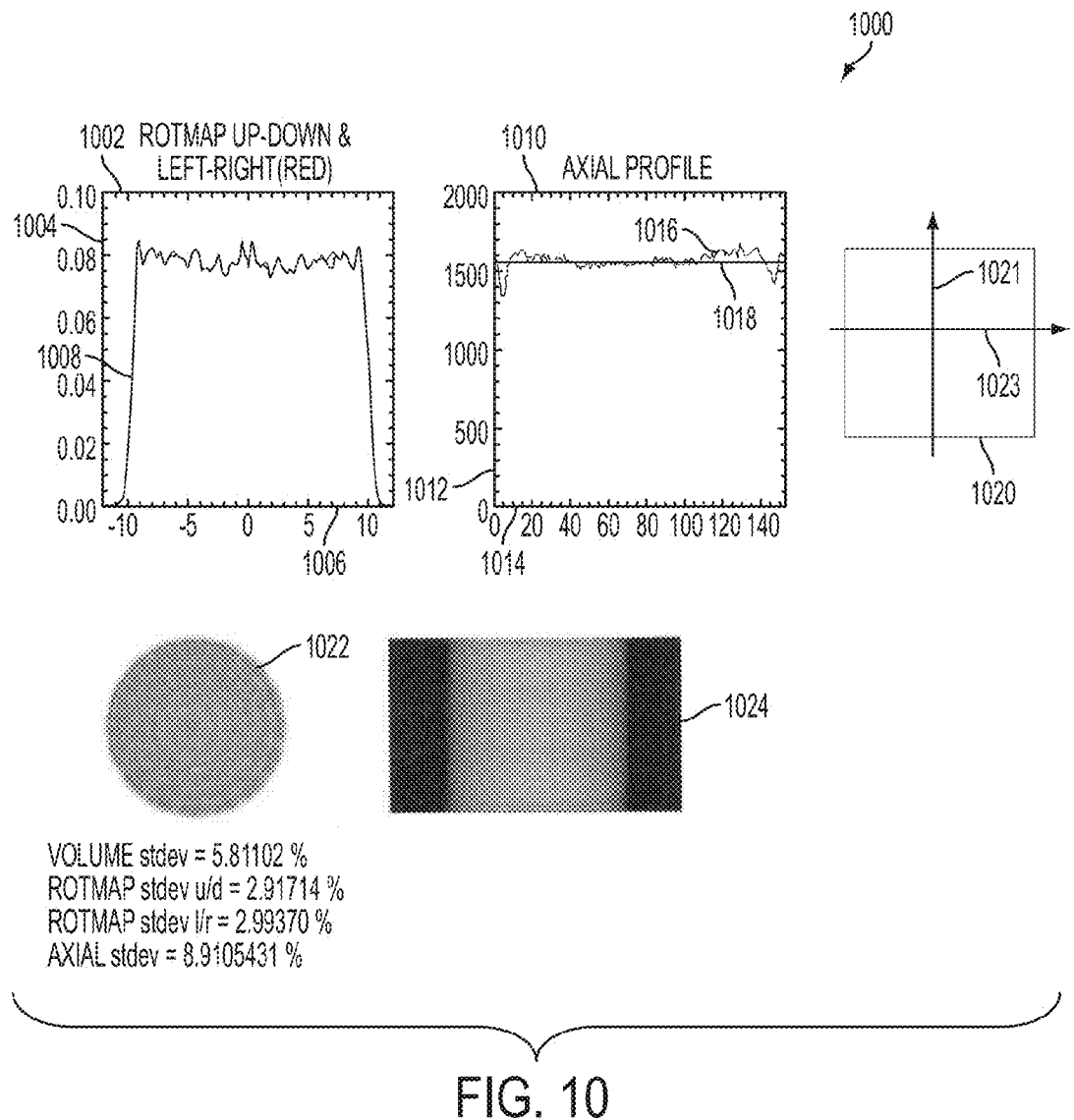
FIG. 10 depicts a $Q_C$ analysis of a device, using 192 blocks, in accordance with embodiments of the invention.

FIG. 10 depicts a $Q_C$ analysis 1000 of a uniform cylindrical phantom of 20 cm diameter placed in the FOV, using emission 192 blocks, in accordance with embodiments of the invention. The $Q_C$ analysis 1000 is used to measure the uniformity of the image. The $Q_C$ analysis 1000 is acquired using 192 detectors and is used to determine the operation condition of the scanner. Specifically, $Q_C$ analysis 1000 is the values of the parameters used to get the corrections for image reconstruction. When reconstructing an image there has to correction for several factors. For example, there has to be random correction, correction for the efficiency of the device, subtraction of scatter, and multiplication by the attenuation. Thereafter, the data is reconstruction into an image.

Specifically, FIG. 10 depicts rotational map 1002, axial profile 1010, cross-section 1020, cross-section 1022, and summation 1024.

Rotational map 1002 depicts values for the upper half, lower half, left side, and right side of the cylinder. The "Y" axis 1004 delineates the number of pixels and the "X" axis delineates the intensity of the signal. The graph 1008 is the circular profile of the object and depicts the intensity of the signal at different points in the cylinder. If the device is working properly there is an expectation that the circular profile is flat.

If the imaging system is correct then all of the planes would have the same intensity. For example, a square that is 256 by 256 and sum all of the voxels in that plane and the sum should be about the same for all of the planes.

Axial profile 1010 depicts data for the cylinder with its axis oriented in the "Z" direction. Along the "Z" axis 1012, of the axial profile 1010, is the intensity of the signal. The "Y" 1014 delineates the plane number. The "Z" direction is the direction in which a patient bed moves. When the circular profile 1104 is flat there is an expectation that the phantom will be flat in the axial direction.

Lead line 1018 delineates an ideal axial profile. Lead line 1016 delineates an actual axial profile. A standard deviation between the ideal and actual axial profiles is calculated.

Cross-section 1020 is a cross section of a cylinder having a plane (shown) parallel to the "Z" axis 1021 and perpendicular to the "X" axis 1023. The cylinder is repeatedly rotated and cross-sections are taken.

Cross-section 1022 is a summation of all of the planes (i.e., slices) from the cylinder rotated around the center of the FOV (i.e., rotated about the Z axis). The cylinder is a function of "X," "Y," and "Z." Rotating the cylinder along the Z axis creates a 2D cylinder (i.e., a disk). Summing the cross-sections amplifies the presence of any artifacts that can be present. An inspection of cross-section 1022 allows a determination whether there are artifacts in the image.

Summation 1024 is a sum of all of the slices integrated in the X direction or in the Y direction (i.e., a summation of the radial profiles rotated about the X axis or the Y axis).

Figure 11:
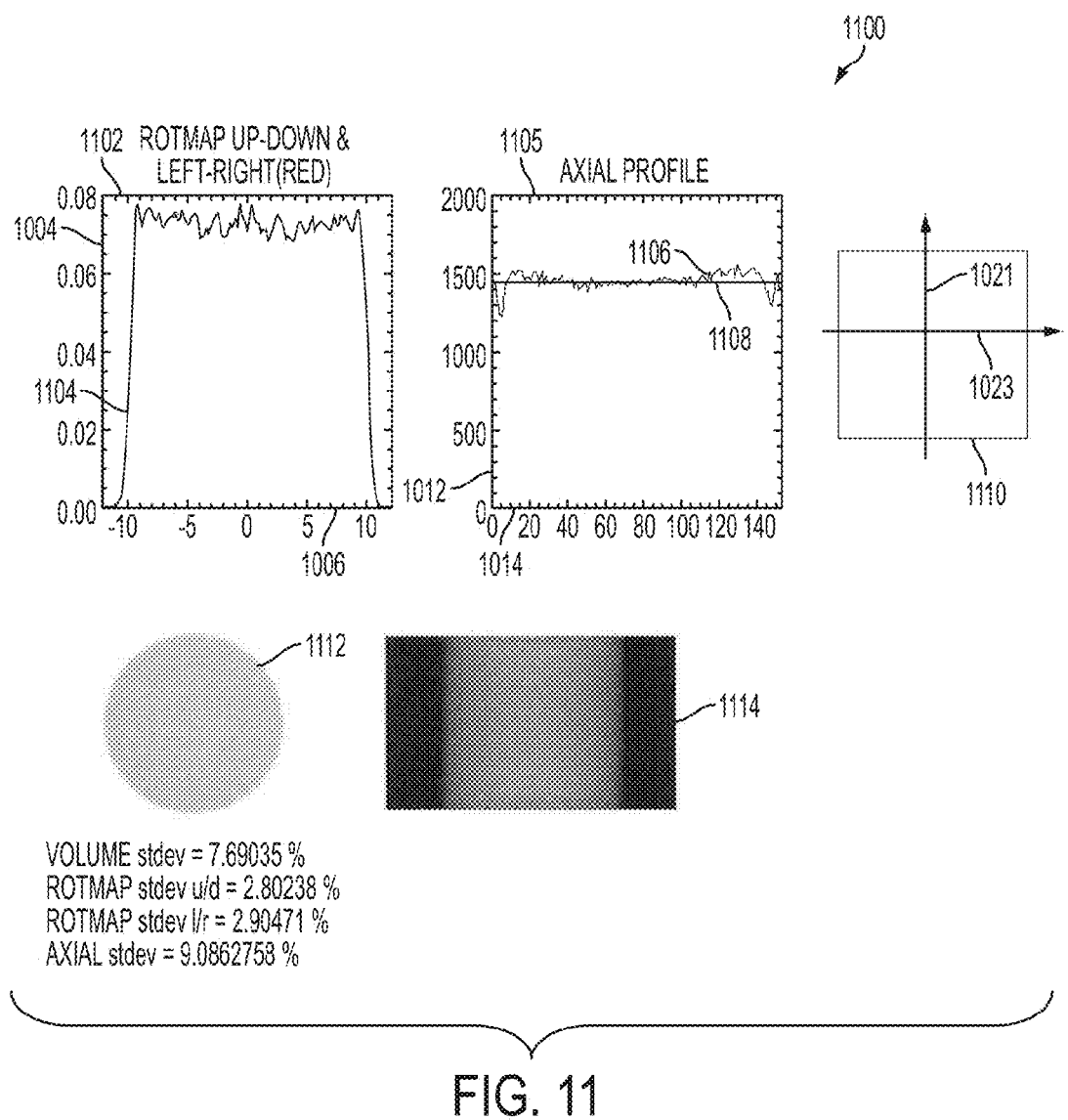
FIG. 11 depicts a $Q_C$ analysis 1100 of a device, using a checkerboard configuration, in accordance with embodiments of the invention.

FIG. 11 depicts a $Q_C$ analysis 1100 of a device, using a checkerboard configuration, in accordance with embodiments of the invention. Lead lines 1004, 1006, 1012, 1014, 1021, and 1023 described above, with respect to FIG. 10, is similarly depicted in FIG. 11. For brevity, a description of these lead lines is not repeated in the description of FIG. 11.

Rotational map 1102 depicts values for the upper half, lower half, left side, and right side of the cylinder. The graph 1104 is the circular profile of the object and depicts the intensity of the signal at different points in the cylinder. If the device is working properly there is an expectation that the circular profile is flat.

If the imaging system is correct then all of the planes would have the same intensity. For example, a square that is 256 by 256 and sum all of the voxels in that plane and the sum should be about the same for all of the planes.

Axial profile 1105 depicts data for the cylinder with its axis oriented in the "Z" direction. When the circular profile 1104 is flat there is an expectation that the phantom will be flat in the axial direction.

Cross-section 1110 is a cross section of a cylinder having a plane (shown) parallel to the "Z" axis 1021 and perpendicular to the "X" axis 1023. The cylinder is repeatedly rotated and cross-sections are taken.

Cross-section 1112 is a summation of all of the planes (i.e., slices) from the cylinder rotated around the center of the FOV (i.e., rotated about the Z axis). The cylinder is a function of "X," "Y," and "Z." Rotating the cylinder along the Z axis creates a 2D cylinder (i.e., a disk). An inspection of cross-section 1112 allows a determination whether there are artifacts in the image.

Summation 1114 is a sum of all of the slices integrated in the X direction or in the Y direction (i.e., a summation of the radial profiles rotated about the X axis or the Y axis).

$Q_C$ analysis 1000 and $Q_C$ analysis 1100 analyze emission blocks. A comparison of the $Q_C$ analysis 1000, in FIG. 10, to the $Q_C$ analysis 1100, in FIG. 1100 shows a substantial similarity (except for increased noise in $Q_C$ analysis 1100 because there is less statistical data in $Q_C$ analysis 1100).

Figure 12:
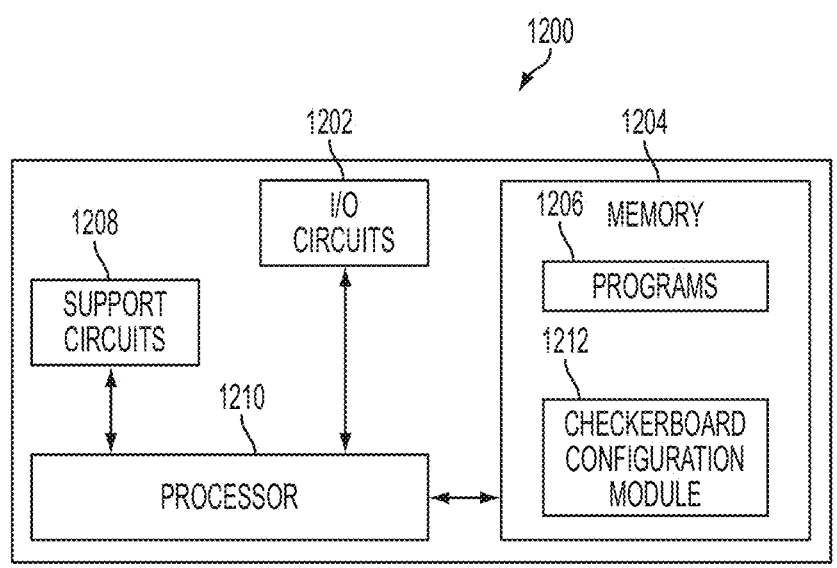
FIG. 12 depicts an embodiment of a high-level block diagram of a general-purpose computer architecture for providing a checkerboard configuration in accordance with embodiments of the invention.

FIG. 12 depicts an embodiment of a high-level block diagram of a general-purpose computer architecture 1200 for providing a checkerboard configuration in accordance with embodiments of the invention. For example, the general-purpose computer 1200 is suitable for use in performing the method of FIG. 5. The general-purpose computer of FIG. 12 includes a processor 1210 as well as a memory 1204 for storing control programs and the like. In various embodiments, memory 1204 also includes programs (e.g., depicted as a "checkerboard configuration module" 1212 for providing a checkerboard configuration in accordance with a sensitivity sufficient for image analysis) for performing the embodiments described herein. The processor 1210 cooperates with conventional support circuitry 1208 such as power supplies, clock circuits, cache memory and the like as well as circuits that assist in executing the software routines 1206 stored in the memory 1204. As such, it is contemplated that some of the process steps discussed herein as software processes can be loaded from a storage device (e.g., an optical drive, floppy drive, disk drive, etc.) and implemented within the memory 1204 and operated by the processor 1210. Thus, various steps and methods of the present invention can be stored on a computer readable medium. The general-purpose computer 1200 also contains input-output circuitry 1202 that forms an interface between the various functional elements communicating with the general-purpose computer 1200.

Although FIG. 12 depicts a general-purpose computer 1200 that is programmed to perform various control functions in accordance with the present invention, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. In addition, although one general-purpose computer 1200 is depicted, that depiction is for brevity on. It is appreciated that each of the methods described herein can be utilized in separate computers.

As previously explained providing a checkerboard configuration having a substantially same FOV as a fully populated scintillator array can be performed by a programmable computer loaded with a software program, firmware, ASIC chip, DSP chip or hardwired digital circuit. Any and all such modifications are intended to be included within the scope of the following claims.

While the foregoing is directed to embodiments of the present invention, other and further embodiments of the invention can be devised without departing from the basic scope thereof, and the scope thereof is determined by the claims that follow.

The invention claimed is:

1. A positron emission tomography (PET) block detector having a plurality of blocks arranged in a two dimensional array, each of the plurality of blocks being of substantially the same size, the PET block detector comprising:
    a plurality of first blocks of said array populated with scintillator block detectors; and
    a plurality of second blocks of said array populated with a component selected from the group of a passive shielding element, a transmission source, and an electromagnetic sensor.

2. The detector of claim 1 wherein said passive shielding is one of lead, tungsten, gold, depleted uranium, and tungsten polymer.

3. The detector of claim 1 wherein up to about one third of said second blocks of said array are populated with passive shielding elements.

4. The detector of claim 1 wherein up to about half of said second blocks of said array are populated with passive shielding elements.

5. The detector of claim 1 wherein up to about one third of said second blocks of said array are populated with transmission sources.

6. The detector of claim 5 wherein said transmission sources are shielded.

7. The detector of claim 1 wherein up to about half of said second blocks of said array are populated with transmission sources.

8. The detector of claim 1 wherein said scintillator block detectors are nuclear emission detectors.

9. The detector of claim 8 wherein said plurality of transmission sources operate simultaneously with said nuclear emission detectors.

10. The detector of claim 1 wherein a transmission source has a decay time of about 2 ns.

11. The detector of claim 1 wherein said detector array is used in one of a time-of-flight (TOF) scanner and a non-TOF scanner.

12. A method of analyzing data from a first positron emission tomography (PET) block detector having a plurality of blocks arranged in a two dimensional array, said plurality of blocks being populated with scintillator block detectors, the method comprising:
    defining a checkerboard configuration for said PET detector, wherein said plurality of blocks of said array are grouped into a first subset of blocks and a second subset of blocks;
    applying said checkerboard configuration to said array;
    acquiring image data from scintillator block detectors corresponding to one of said first and second subsets in accordance with said applied checkerboard configuration, for use in image reconstruction; and ignoring image data from scintillator block detectors corresponding to the other of said first and second subsets in accordance with said applied checkerboard configuration, such that image data from the ignored subset of scintillator block detectors is not used in image reconstruction.

13. A positron emission tomography (PET) block detector having a plurality of blocks arranged in a two dimensional array, each of the plurality of blocks being of substantially the same size, the PET block detector comprising:
  a plurality of first blocks of said array populated with scintillator block detectors; and
  a plurality of second blocks of said array populated with passive shielding elements.

* * * * *